(12) United States Patent
Lee

(10) Patent No.: US 11,103,621 B2
(45) Date of Patent: Aug. 31, 2021

(54) DISCHARGE SOLIDIFIER AND MALODOUR CONTROL

(71) Applicant: ConvaTec Limited, Deeside (GB)

(72) Inventor: Stewart Lee, Lancashire (GB)

(73) Assignee: CONVATEC LTD, Bridgewater, NJ (US)

(*) Notice: Subject to any disclaimer, the term of this patent is extended or adjusted under 35 U.S.C. 154(b) by 738 days.

(21) Appl. No.: 15/882,916

(22) Filed: Jan. 29, 2018

(65) Prior Publication Data

US 2018/0147325 A1    May 31, 2018

Related U.S. Application Data

(63) Continuation of application No. 14/347,970, filed as application No. PCT/GB2012/052133 on Aug. 31, 2012, now abandoned.

(30) Foreign Application Priority Data

Sep. 2, 2011    (GB) .................................... 1115160

(51) Int. Cl.
*A61F 5/445*   (2006.01)
*A61L 28/00*   (2006.01)
*A61F 5/441*   (2006.01)

(52) U.S. Cl.
CPC .......... *A61L 28/0092* (2013.01); *A61F 5/441* (2013.01); *A61L 28/0003* (2013.01); *A61L 28/0011* (2013.01); *A61F 5/445* (2013.01)

(58) Field of Classification Search
None
See application file for complete search history.

(56) References Cited

U.S. PATENT DOCUMENTS

| 4,104,294 | A | * | 8/1978 | Grose ................... B01J 29/035 |
| | | | | 423/335 |
| 4,546,143 | A | | 10/1985 | Weil et al. |
| 4,795,482 | A | * | 1/1989 | Gioffre .................. B01D 53/02 |
| | | | | 95/141 |
| 4,826,497 | A | * | 5/1989 | Marcus .................... B01J 20/18 |
| | | | | 604/359 |
| 5,019,062 | A | * | 5/1991 | Ryan .................. A61F 13/8405 |
| | | | | 604/359 |

(Continued)

FOREIGN PATENT DOCUMENTS

| EP | 0347746 A1 | 12/1989 |
| EP | 1690553 A1 | 8/2006 |

(Continued)

OTHER PUBLICATIONS

US 10,806,622 B2, 10/2020, Hansen et al. (withdrawn)

(Continued)

*Primary Examiner* — Peter A Salamon
(74) *Attorney, Agent, or Firm* — Taft Stettinius & Hollister LLP

(57) ABSTRACT

An ostomy bag insert (104) comprising a polyacrylate superabsorbent (300) and a powdered zeolite (301). The ostomy bag insert is configured to absorb fluids excreted by the body and to control odours resultant from the excreted matter within the ostomy bag (100). The present zeolite exhibits enhanced odour control.

27 Claims, 8 Drawing Sheets

(56) References Cited

U.S. PATENT DOCUMENTS

| | | | |
|---|---|---|---|
| 5,306,487 A * | 4/1994 | Karapasha | A61L 15/18 424/76.6 |
| 5,817,300 A * | 10/1998 | Cook | A61F 5/441 424/66 |
| 5,860,959 A * | 1/1999 | Gent | A61F 5/441 604/327 |
| 6,059,860 A * | 5/2000 | Larson | B01D 53/261 95/117 |
| 6,245,693 B1 * | 6/2001 | Gagliardi | A61F 13/8405 442/59 |
| 6,329,465 B1 | 12/2001 | Takahashi et al. | |
| 6,485,476 B1 | 11/2002 | Von Dyck et al. | |
| 6,605,304 B1 * | 8/2003 | Wellinghoff | A61L 2/20 424/489 |
| 6,617,016 B2 | 9/2003 | Zhang et al. | |
| 6,649,805 B1 * | 11/2003 | Carlucci | A61L 15/18 604/359 |
| 6,852,100 B1 * | 2/2005 | Gent | A61F 5/441 604/333 |
| 6,946,182 B1 | 9/2005 | Allgeuer et al. | |
| 6,946,522 B2 | 9/2005 | Jacob et al. | |
| 7,056,971 B2 | 6/2006 | Varma | |
| 7,060,753 B2 | 6/2006 | Jacob et al. | |
| 7,629,406 B2 | 12/2009 | Qian et al. | |
| 8,449,513 B2 | 5/2013 | Abrams | |
| 8,979,811 B2 | 3/2015 | Keleny et al. | |
| 9,968,480 B2 | 5/2018 | Nyberg | |
| 10,278,857 B2 | 5/2019 | Hansen et al. | |
| D862,691 S | 10/2019 | Fenton | |
| 10,434,015 B2 | 10/2019 | Taylor et al. | |
| 10,434,309 B2 | 10/2019 | Forsell | |
| 10,449,081 B2 | 10/2019 | Lee | |
| 10,449,082 B2 | 10/2019 | Johnsen | |
| 10,463,527 B2 | 11/2019 | Gallant et al. | |
| 10,470,917 B2 | 11/2019 | Chang | |
| 10,470,918 B2 | 11/2019 | Bendix | |
| 10,471,173 B2 | 11/2019 | Misawa | |
| 10,478,328 B2 | 11/2019 | Guidry et al. | |
| 10,478,329 B2 | 11/2019 | Oberholtzer et al. | |
| 10,478,330 B2 | 11/2019 | Wiltshire et al. | |
| 10,500,084 B2 | 12/2019 | Hansen et al. | |
| 10,500,315 B2 | 12/2019 | Chang et al. | |
| 10,507,318 B2 | 12/2019 | Jin et al. | |
| 10,512,562 B2 | 12/2019 | Kavanagh et al. | |
| 10,524,953 B2 | 1/2020 | Hanuka et al. | |
| 10,531,978 B2 | 1/2020 | Haas et al. | |
| 10,537,461 B2 | 1/2020 | Hanuka et al. | |
| 10,537,462 B1 | 1/2020 | Hatchett et al. | |
| 10,583,029 B2 | 3/2020 | Chang | |
| 10,588,773 B2 | 3/2020 | Tsai et al. | |
| 10,610,402 B1 | 4/2020 | Idowu et al. | |
| 10,617,554 B2 | 4/2020 | Luce | |
| 10,617,555 B2 | 4/2020 | James et al. | |
| 10,646,370 B2 | 5/2020 | Keleny et al. | |
| 10,653,551 B2 | 5/2020 | Apolinario et al. | |
| 10,660,784 B2 | 5/2020 | Nishtala et al. | |
| 10,660,785 B2 | 5/2020 | Kaufman et al. | |
| 10,660,786 B2 | 5/2020 | Obst et al. | |
| 10,729,806 B2 | 8/2020 | Bingol et al. | |
| 10,736,769 B2 | 8/2020 | Grove Sund et al. | |
| 10,744,224 B2 | 8/2020 | Israelson et al. | |
| 10,758,398 B2 | 9/2020 | Murthy Aravalli et al. | |
| 10,779,986 B2 | 9/2020 | Cox | |
| 10,799,385 B2 | 10/2020 | Hansen et al. | |
| 10,813,786 B2 | 10/2020 | Lysgaard | |
| 10,813,787 B2 | 10/2020 | Dinakara et al. | |
| 2002/0055594 A1 * | 5/2002 | Roux | B01J 20/28014 525/329.7 |
| 2002/0114958 A1 * | 8/2002 | Ozeki | B01J 20/28033 428/446 |
| 2002/0142937 A1 * | 10/2002 | Carter | C11D 17/046 510/507 |
| 2003/0158296 A1 * | 8/2003 | Brehm | C08K 3/34 523/218 |
| 2004/0267216 A1 | 12/2004 | Udayakumar et al. | |
| 2006/0058576 A1 | 3/2006 | Davies et al. | |
| 2006/0173430 A1 * | 8/2006 | Lee | A61L 28/0049 604/368 |
| 2007/0237916 A1 | 10/2007 | Rasmussen et al. | |
| 2008/0103463 A1 | 5/2008 | Tsai et al. | |
| 2009/0088711 A1 | 4/2009 | Shelley et al. | |
| 2009/0216207 A1 | 8/2009 | Nielsen | |
| 2010/0174253 A1 | 7/2010 | Cline et al. | |
| 2011/0052737 A1 | 3/2011 | Florence et al. | |
| 2011/0218507 A1 | 9/2011 | Andersen et al. | |
| 2012/0041400 A1 | 2/2012 | Christensen | |
| 2012/0109086 A1 | 5/2012 | Tsai | |
| 2012/0136324 A1 | 5/2012 | Hanuka et al. | |
| 2012/0179124 A1 | 7/2012 | Nguyen-Demary et al. | |
| 2012/0190900 A1 * | 7/2012 | Weston | B01J 20/186 568/916 |
| 2013/0072886 A1 | 3/2013 | Schertiger et al. | |
| 2013/0226063 A1 | 8/2013 | Taylor et al. | |
| 2014/0207094 A1 | 7/2014 | Chang | |
| 2014/0221950 A1 | 8/2014 | Chang et al. | |
| 2014/0288517 A1 | 9/2014 | Tsai et al. | |
| 2014/0316360 A1 | 10/2014 | Ekfeldt et al. | |
| 2015/0133881 A1 | 5/2015 | Freiding | |
| 2015/0209172 A1 | 7/2015 | Richmann et al. | |
| 2016/0151198 A1 | 6/2016 | Frampton et al. | |
| 2016/0193003 A1 | 7/2016 | Todd et al. | |
| 2016/0206469 A1 | 7/2016 | Prezelin | |
| 2017/0007440 A1 | 1/2017 | Moavenian | |
| 2017/0065451 A1 | 3/2017 | Brandt et al. | |
| 2017/0209295 A1 | 7/2017 | Smith et al. | |
| 2017/0209296 A1 | 7/2017 | Cailleteau | |
| 2018/0064572 A1 | 3/2018 | Wiltshire | |
| 2018/0147325 A1 * | 5/2018 | Lee | A61L 28/0003 |
| 2018/0235801 A1 | 8/2018 | Oellgaard et al. | |
| 2018/0236207 A1 | 8/2018 | Shankarsetty | |
| 2018/0303655 A1 | 10/2018 | Glithero et al. | |
| 2018/0311066 A1 | 11/2018 | Hansen et al. | |
| 2018/0344506 A1 | 12/2018 | Larsen | |
| 2018/0360644 A1 | 12/2018 | Alvarez Ponce | |
| 2018/0369474 A1 | 12/2018 | Falleboe et al. | |
| 2019/0015241 A1 | 1/2019 | Lin et al. | |
| 2019/0029868 A1 | 1/2019 | Grum-Schwensen et al. | |
| 2019/0110919 A1 | 4/2019 | Beckers et al. | |
| 2019/0117824 A1 | 4/2019 | Hansen et al. | |
| 2019/0247549 A1 | 8/2019 | Nielsen | |
| 2019/0328571 A1 | 10/2019 | Adachi | |
| 2019/0328572 A1 | 10/2019 | Weinberg et al. | |
| 2019/0365560 A1 | 12/2019 | Timms et al. | |
| 2019/0374372 A1 | 12/2019 | Seres et al. | |
| 2019/0380860 A1 | 12/2019 | Eggert et al. | |
| 2019/0380861 A1 | 12/2019 | Nordquist et al. | |
| 2019/0380882 A1 | 12/2019 | Taylor et al. | |
| 2020/0015996 A1 | 1/2020 | Schertiger | |
| 2020/0030134 A1 | 1/2020 | Hopper | |
| 2020/0038226 A1 | 2/2020 | Botten et al. | |
| 2020/0046541 A1 | 2/2020 | Sund et al. | |
| 2020/0046542 A1 | 2/2020 | Guidry et al. | |
| 2020/0046543 A1 | 2/2020 | Scalise et al. | |
| 2020/0054478 A1 | 2/2020 | Forsell | |
| 2020/0060863 A1 | 2/2020 | Sund et al. | |
| 2020/0061282 A1 | 2/2020 | Hvid et al. | |
| 2020/0069455 A1 | 3/2020 | Oberholtzer et al. | |
| 2020/0078206 A1 | 3/2020 | Chiladakis | |
| 2020/0100931 A1 | 4/2020 | Schoess et al. | |
| 2020/0100946 A1 | 4/2020 | Wohlgemuth et al. | |
| 2020/0138619 A1 | 5/2020 | Cisko, Jr. et al. | |
| 2020/0146944 A1 | 5/2020 | Moulton et al. | |
| 2020/0163792 A1 | 5/2020 | Schertiger | |
| 2020/0164196 A1 | 5/2020 | Jin et al. | |
| 2020/0188160 A1 | 6/2020 | Udayakumar | |
| 2020/0197213 A1 | 6/2020 | Frampton-Vallance et al. | |
| 2020/0214872 A1 | 7/2020 | Tretheway et al. | |
| 2020/0214873 A1 | 7/2020 | Tretheway et al. | |
| 2020/0214875 A1 | 7/2020 | Tretheway et al. | |
| 2020/0229962 A1 | 7/2020 | Torstensen et al. | |
| 2020/0246173 A1 | 8/2020 | Schertiger et al. | |
| 2020/0261254 A1 | 8/2020 | Williams et al. | |
| 2020/0276044 A1 | 9/2020 | Tretheway et al. | |

(56) References Cited

U.S. PATENT DOCUMENTS

| | | |
|---|---|---|
| 2020/0276045 A1 | 9/2020 | Bendavit |
| 2020/0281758 A1 | 9/2020 | Tan |
| 2020/0281761 A1 | 9/2020 | Tretheway et al. |
| 2020/0289307 A1 | 9/2020 | Tretheway et al. |
| 2020/0289308 A1 | 9/2020 | Tretheway et al. |
| 2020/0297524 A1 | 9/2020 | Hunt et al. |
| 2020/0306073 A1 | 10/2020 | Olsen et al. |
| 2020/0306074 A1 | 10/2020 | Speiermann et al. |
| 2020/0330258 A1 | 10/2020 | Hansen et al. |
| 2020/0330259 A1 | 10/2020 | Sund et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0338230 A1 | 10/2020 | Israelson et al. |

FOREIGN PATENT DOCUMENTS

| | | |
|---|---|---|
| GB | 2259858 A | 3/1993 |
| GB | 2329339 A | 3/1999 |
| GB | 2534012 A | 7/2016 |
| GB | 2544180 A | 5/2017 |
| GB | 2548673 A | 9/2017 |
| GB | 2550936 A | 12/2017 |
| JP | S59151965 A | 8/1984 |
| JP | H0924580 A | 1/1997 |
| JP | 2001061886 A | 3/2001 |
| JP | 2005307049 A | 11/2005 |
| JP | 2005533618 A | 11/2005 |
| KR | 0157598 B1 | 2/1999 |
| WO | WO-9112029 A1 | 8/1991 |
| WO | WO-2009144486 A2 | 12/2009 |
| WO | WO-2013030581 A1 | 3/2013 |
| WO | WO-2013043226 A1 | 3/2013 |
| WO | 2015110544 A1 | 7/2015 |
| WO | 2015138190 A1 | 9/2015 |
| WO | 2015148035 A1 | 10/2015 |
| WO | 2018188706 A1 | 10/2018 |
| WO | 2018188707 A1 | 10/2018 |
| WO | 2019058126 A1 | 3/2019 |
| WO | 2019058127 A1 | 3/2019 |
| WO | 2019091526 A1 | 5/2019 |
| WO | 2019091527 A1 | 5/2019 |
| WO | 2019091528 A1 | 5/2019 |
| WO | 2019091529 A1 | 5/2019 |
| WO | 2019091532 A1 | 5/2019 |
| WO | 2019099662 A1 | 5/2019 |
| WO | 2019120424 A1 | 6/2019 |
| WO | 2019120429 A1 | 6/2019 |
| WO | 2019120430 A1 | 6/2019 |
| WO | 2019120432 A1 | 6/2019 |
| WO | 2019120433 A1 | 6/2019 |
| WO | 2019120434 A1 | 6/2019 |
| WO | 2019120437 A1 | 6/2019 |
| WO | 2019120438 A1 | 6/2019 |
| WO | 2019120439 A1 | 6/2019 |
| WO | 2019120442 A1 | 6/2019 |
| WO | 2019120443 A1 | 6/2019 |
| WO | 2019120444 A1 | 6/2019 |
| WO | 2019120446 A1 | 6/2019 |
| WO | 2019120448 A1 | 6/2019 |
| WO | 2019120449 A1 | 6/2019 |
| WO | 2019120450 A1 | 6/2019 |
| WO | 2019120451 A1 | 6/2019 |
| WO | 2019120452 A1 | 6/2019 |
| WO | 2019120458 A1 | 6/2019 |

OTHER PUBLICATIONS

Therapeutic Mouthrinsing: An Effective Component to Oral Hygiene, Hughes et al., Oct. 20, 2016, p. 3 (Year: 2016).*
Acquarulo and O'Neil, Advances in compounding medical plastics with nanoclay fillers are pushing the materials envelope for minimally invasive devices. Enhancing Medical Device Performance with Nanocomposite Polymers, posted May, 1, 2002, 4 pages. [Retrieved on Jan. 14, 2016; Retrieved from the Internet: http://www.mddionline.com/article/enhancing-medical-device-performance-nanocomposite-polymers.
Australian Patent Application No. 2016228205 Examination Report No. 1 dated Jun. 7, 2017.
Australian Patent Application No. 2016228205 Examination Report No. 2 dated May 29, 2018.
Australian Patent Application No. 2012313393 Examiner's Second Report dated Sep. 1, 2016.
Canadian Patent Application No. 2,834,848 Office Action dated Apr. 3, 2018.
Canadian Patent Application No. 2,850,589 Examination Report dated Aug. 23, 2018.
Chinese Patent Application No. 201280021995.9 Decision of Rejection dated Sep. 14, 2016.
Chinese Patent Application No. 201280021995.9 Decision on Reexamination dated Jan. 3, 2018.
Chinese Patent Application No. 201280021995.9 Office Action dated May 25, 2017.
Chinese Patent Application No. 201280054020.6 Third Office Action dated Jul. 27, 2016.
European Patent Application No. 12756241.1 Communication dated Sep. 7, 2016.
European Patent Application No. 12833128.7 Communication dated Aug. 31, 2016.
Japanese Patent Application No. 2013-558199 Office Action dated Apr. 4, 2017.
Japanese Patent Application No. 2013-558199 Office Action dated Sep. 6, 2016.
Korean Patent Application No. 10-2014-7008715 Preliminary Rejection dated Sep. 27, 2018.
Mexican Patent Application No. MX/a/2015/015197 Office Action dated Mar. 2, 2018.
New Zealand Patent Application No. 712149 Examiner's second report dated Mar. 8, 2017.
New Zealand Patent Application No. 712149 Further Examination Report dated May 2, 2017.
PCT/GB2012/052133 International Preliminary Report on Patentability dated Mar. 4, 2014.
PCT/GB2012/052133 International Search Report and Written Opinion dated Dec. 14, 2012.
PCT/US2012/29375 International Preliminary Report on Patentability dated Sep. 17, 2013.
PCT/US2012/29375 International Search Report and Written Opinion dated Jun. 12, 2012.
Russian Patent Application No. 2014112699 Official Action Aug. 22, 2016.
U.S. Appl. No. 14/005,814 Office Action dated Feb. 28, 2017.
U.S. Appl. No. 14/005,814 Office Action dated Jan. 5, 2018.
U.S. Appl. No. 14/005,814 Office Action dated Jun. 16, 2016.
U.S. Appl. No. 14/005,814 Office Action dated Jun. 16, 2017.
U.S. Appl. No. 14/005,814 Office Action dated Sep. 29, 2016.
U.S. Appl. No. 14/347,970 Office Action dated Jun. 30, 2017.
U.S. Appl. No. 14/347,970 Office Action dated Nov. 30, 2016.

* cited by examiner

DISCHARGE SOLIDIFIER AND MALODOUR CONTROL

CROSS-REFERENCE

This application is a continuation application of Ser. No. 14/347,970, filed on Jul. 15, 2014, which is a U.S. National Phase Application of PCT/GB2012/052133, filed Aug. 31, 2012, which claims priority to GB 1115160.2, filed Sep. 2, 2011, which is incorporated herein by reference in its entirety and to which application we claim priority under 35 USC § 120.

The present invention relates to a superabsorbent and malodour control composition and in particular, although not exclusively, to a superabsorbent for solidifying collected matter excreted by the body and a control agent for controlling odours associated with the excreted matter.

Ostomy patients typically wear an ostomy bag into which body waste is excreted. Ostomy patients fall into three categories, each category necessitating the patient wearing an ostomy bag. Firstly, urostomy patients typically have had their bladders removed. Accordingly in this case, urine is passed through the stoma and into the ostomy bag. Secondly, colostomy patients have undergone surgery to remove all or part of the colon necessitating an ostomy bag to collect both liquid and solid excreted matter. Thirdly, ileostomy patients similarly rely upon an ostomy bag to collect excreted matter which is redirected through the abdominal wall.

Generally an ostomy bag comprises an opening which is sealed against the patient's skin around the surgically created body orifice, termed a stoma. Many ostomy bags are provided with a discharge outlet to allow excreted matter to be emptied from the ostomy bag by the patient.

When body waste is excreted into the ostomy bag it continues to release malodours which are unpleasant and can cause embarrassment to the patient. Also, where the excreted matter is in liquid form, leakage from the ostomy bag is a potential risk which would also cause embarrassment to the patient.

A number of additives have been proposed for ostomy bags designed to solidify excreted fluid matter and reduce unpleasant malodours. US 2002/0055594 discloses a superabsorbent tablet configured to thicken body excretions. The tablet comprises a superabsorbent polymer in the form of cross linked sodium or calcium polyacrylate designed to provide quick gelling of the ostomy bag contents following excretion.

U.S. Pat. No. 6,852,100 also discloses an ostomy pouch configured to reduce unpleasant odours. Superabsorbent fibres are used in combination with a malodour counteractant selected from various different categories of odour controlling (masking and neutralising) agents including for example hydrogen peroxide and bacterial growth inhibitors such as sodium nitrate and benzyl alkonium chloride.

GB 2329339 discloses a superabsorbent for an ostomy bag comprising granules of a superabsorbent formed into a stick or rod and housed within a water soluble outer sleeve. Odour counteractants, disinfectants and preservatives are also incorporated within the ostomy bag insert.

U.S. Pat. No. 5,860,959 discloses a hydroscopic composition to reduce malodours from an ostomy bag. Water absorbing materials such as starch or alkaline metal polyacrylates are employed as superabsorbents in combination with odour counteractants such as volcanic clays and activated carbon granules.

However, there exists a need for an ostomy bag insert configured to effectively solidify or gel excreted matter and control unwanted malodours.

The inventors provide a superabsorbent material for positioning within a stoma bag exhibiting superabsorbent and odour controlling properties. The superabsorbent blend has been found to exhibit enhanced malodour reduction over existing ostomy bag inserts.

According to a first aspect of the present invention there is provided an ostomy bag insert comprising: a polyacrylate superabsorbent; and a powdered zeolite; wherein the superabsorbent is coated with the powdered zeolite.

Reference within the specification to zeolite includes zeolites being microporous and capable of accommodating within their structure molecular species including ions and in particular odorous compounds typically found in faecal waste.

Optionally, the zeolite may comprise a naturally sourced zeolite mineral including in particular analcime, chabazite, clinoptilolite, heulandite, natrolite, phillipsite, and stilbite.

Optionally, the zeolite is a zeolite blend comprising a hydrophilic and a hydrophobic zeolite. Alternatively, the zeolite may be substantially hydrophilic or substantially hydrophobic. A preferred hydrophobic zeolite comprises an ammonium zeolite being a zeolite having ammonium groups forming part of the zeolite structure. A preferred hydrophilic zeolite comprises a sodium aluminosilicate.

Optionally, the insert may further comprise powdered activated carbon. Preferably the insert comprises the zeolite as a major component and activated carbon as a minor component based on a dry weight percentage. Optionally, a weight % ratio of the activated carbon to the zeolite or zeolite blend, as part of the insert, is in the range 0.01:1 to 0.05:1.

The powdered zeolite may comprise a particle size equal to or less than 0.15 mm and/or 0.045 mm and/or 0.075 mm. Optionally, the zeolite comprises a surface area of substantially 400 $m^2/g$.

Preferably, 99% by weight of the zeolite may comprise a particle size equal to or less than 0.15 mm; 95% by weight of the zeolite may comprise a particle size equal to or less than 0.075 mm and 90% by weight of the zeolite may comprise a particle size equal to or less than 0.045 mm.

Preferably, the activated carbon comprises and is derived from coconut shell char. The activated carbon may comprise a surface area of substantially 1250 $m^2/g$. Preferably, the polyacrylate superabsorbent comprises a granular configuration being at least one or a multiple order of magnitude greater in size than the particle size of the zeolite or activated carbon.

Synergistically, the zeolite and optionally the activated carbon may be bound to the superabsorbent granules by electrostatic forces. The superabsorbent may comprise sodium or calcium polyacrylate. Optionally, the zeolite and/or the activated carbon may comprise any metal impregnated activated charcoal.

Preferably, the superabsorbent and powdered zeolite or zeolite blend is housed within a water soluble paper sachet. The paper sachet may comprise sodium carboxy methyl cellulose and wood pulp. The edges of the sachet may be heat sealed so as to trap the granular superabsorbent and zeolite within the envelope formed by the soluble paper.

Alternatively, the zeolite or zeolite based blend may be encased within water soluble films (e.g. PVA films), gel caps, plastic straws/wands or formed as tablets. Moreover, the insert may comprise a plurality of separate units (e.g.

tablets, gel caps, sachets). These units would then be inserted separately into the ostomy bag.

According to a second aspect of the present invention there is provided an ostomy bag comprising an insert as described herein. The insert may be permanently or temporarily attached to an internal wall of the ostomy bag using conventional means found in the art. For example, the insert may be attached to the internal walls via a flap, strap or permeable pouch or cover allowing release of the superabsorbent and odour absorbing material upon contact with the excreted body fluid.

Preferably, the insert comprises 1,000 mg to 10,000 mg of the polyacrylate superabsorbent and 25 mg to 5,000 mg of the zeolite or zeolite blend.

A specific implementation of the invention will now be described by way of example only, and with reference to the attached drawings in which.

The inventors provide a material blend configured to solidify excreted matter within an ostomy bag and to reduce odours within the ostomy bag which would otherwise be released from the bag when it is emptied by a patient. A material blend is housed within a water soluble sachet which provides a convenient means by which the liquid and odour absorbing material blend may be stored and transported prior to use within the ostomy bag. The dissolvable sachet may be used in all manner of pouches or bags designed for collecting body excretions such as ostomy, drainage bags or other applications where body fluids require thickening or gelling and odour control (neutralisation/absorption).

Figure 1:
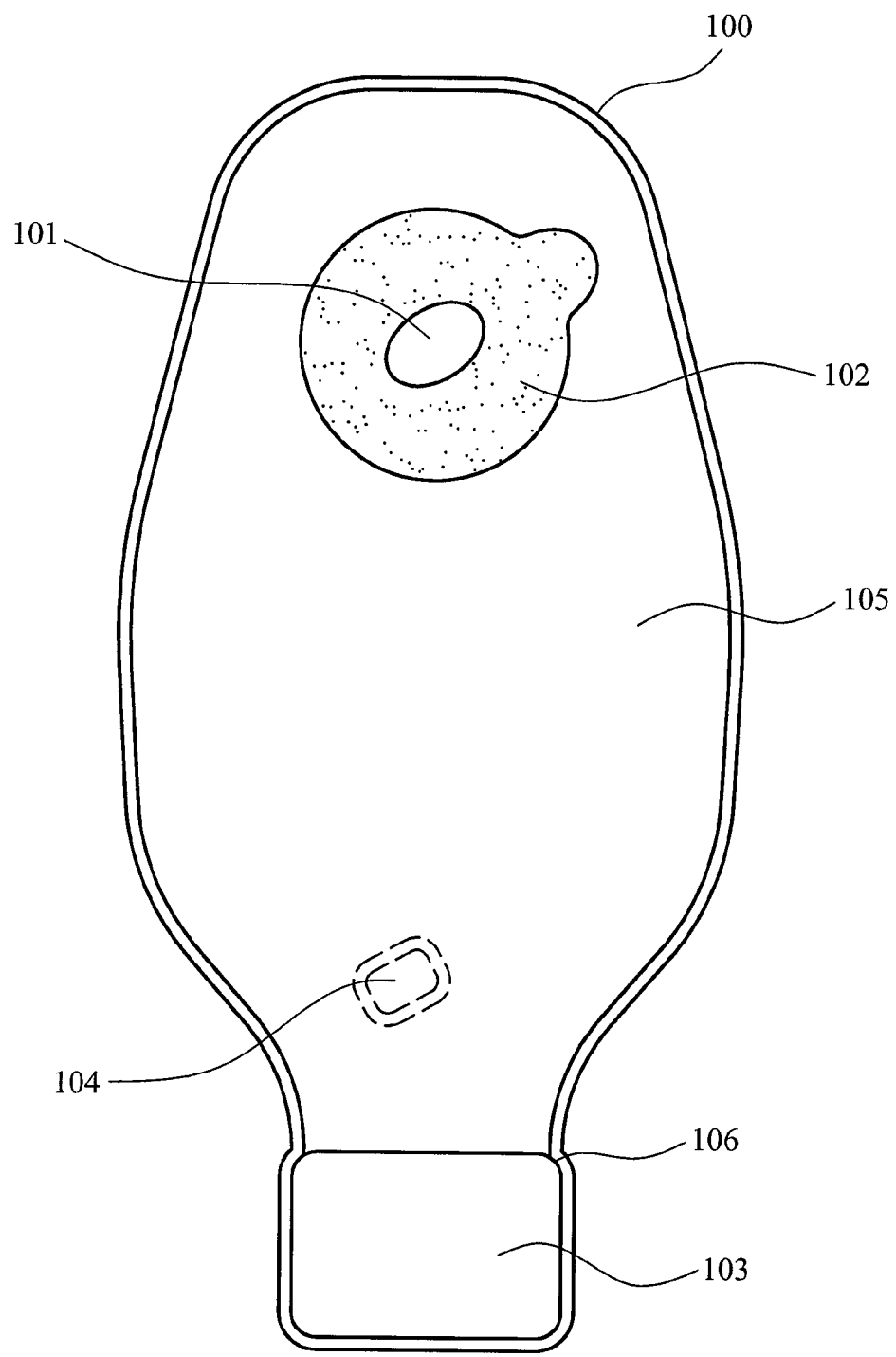
FIG. 1 illustrates an ostomy bag comprising an insert configured to solidify liquid matter within the ostomy bag and control and reduce malodours according to a specific implementation of the present invention.

FIG. 1 illustrates an ostomy bag 100 comprising an internal chamber 105 and an inlet opening 101 surrounded by an annular adhesive pad 102. A drainage flap 103 is provided at a lower region 106 of bag 100. An odour controlling and liquid superabsorbent insert 104 is housed within internal chamber 105 and is dimensioned so as to pass through inlet opening 101 during initial insertion prior to attachment of bag 100 and through outlet opening 103 after empty and reuse of bag 100.

In use, ostomy bag 100 is secured to the skin of a patient at the abdominal region, via adhesive pad 102 such that inlet opening 101 is aligned with the stoma site formed in the patient. Accordingly, excreted matter passes through the stoma and into internal chamber 105 of ostomy bag 100 via inlet opening 101.

The excreted body fluid contacts insert 104 which acts to gel (partially solidify) the fluid matter and control malodours within internal chamber 105.

Following solidification of the excreted matter, the contents of the ostomy bag 100 may then be emptied via the flap arrangement 103 configured to dispense liquid and/or solid from internal chamber 105. Flap 103 may comprise any conventional tap or flap design configured to allow liquid and/or solid matter to be released from internal chamber 105. Following emptying of the bag, a new insert may then be inserted into internal chamber 105 via the flap 103 such that a user is not required to detach bag 100 from positioning around the stoma.

Figure 2:
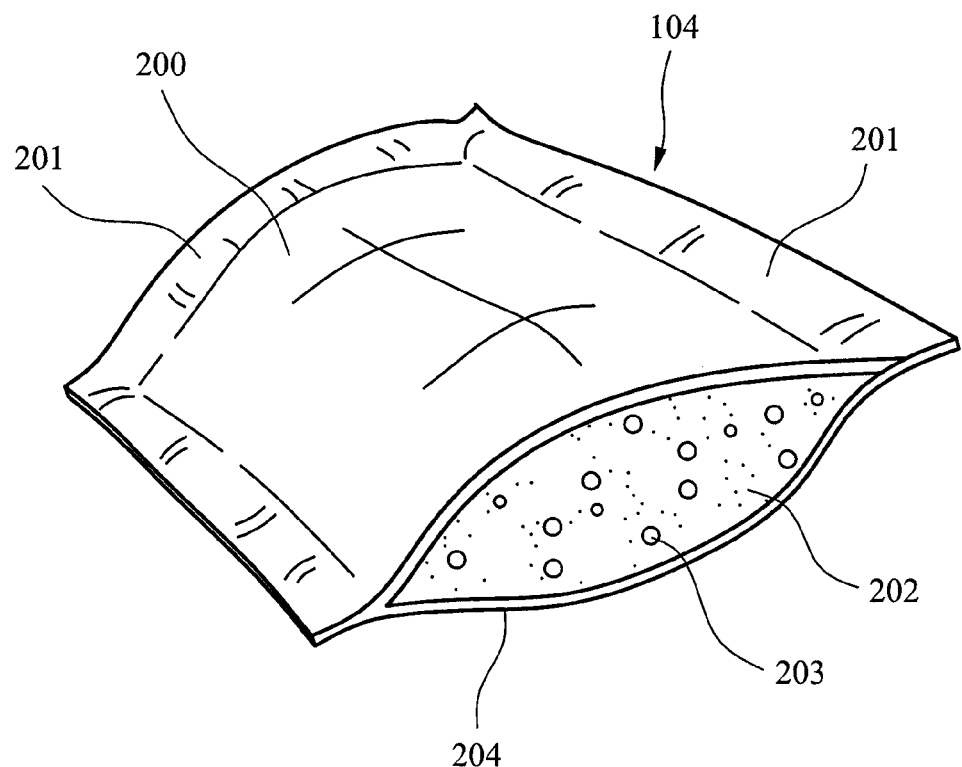
FIG. 2 illustrates a partial cut-away view of the ostomy bag insert of FIG. 1 formed as a sachet containing a granular and powdered material.
Figure 3:
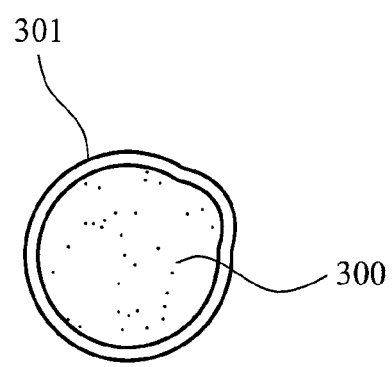
FIG. 3 illustrates a superabsorbent granule coated with a zeolite material.

Referring to FIGS. 2 and 3, insert 104 is formed as a sachet comprising a water soluble paper having an upper layer 200 and a lower opposed layer 204. The edges of the upper and lower layers 200, 204 are heat sealed 201 to define an internal cavity 202 sealed along all four edges of the rectangular sachet. Insert 104 comprises liquid and odour absorbing material blend 203 (comprising a polyacrylate based superabsorbent 300 and a powdered zeolite 301) housed within internal cavity 202 formed by the upper and lower layers 200, 203. As will be appreciated by those skilled in the art, the present invention may comprise any specific polyacrylate comprising superabsorbent properties suitable for use to absorb fluids, excreted by the human body. The zeolite may comprise any natural or synthetic zeolite or zeolite composite or blend configured to control malodours of the type associated with human body excreted matter. It is preferred that the zeolite is a blend of a hydrophobic and a hydrophilic zeolite, Referring to FIG. 3, it has been found advantageous for malodour control/reduction to coat the superabsorbent 300 with the zeolite 301. In particular, the superabsorbent, according to a specific implementation of the present invention, is formed as granules or pellets. In this configuration, the finely powdered zeolite readily coats the external surface of the granules or pellets providing an active blend exhibiting enhanced odour control over existing stoma bag inserts. The powdered zeolite may be maintained at the outer surface of the superabsorbent granules by, in part, the electrostatic interactions between the superabsorbent and the powdered zeolite.

According to one embodiment, the stoma bag insert 104 comprises a sodium polyacrylate superabsorbent 300. The water soluble sachet comprises sodium carboxy methyl cellulose and wood pulp comprising a thickness in a range 0.07 mm to 0.09 mm. The zeolite comprises a zeolite blend having a hydrophilic zeolite component and a hydrophobic zeolite component. The water soluble sachet comprises 2 g of sodium polyacrylate and 250 mg of zeolite.

According to a further specific embodiment, the insert 104 comprises sodium polyacrylate superabsorbent 300, the same water soluble sachet as described above, a zeolite blend having a hydrophilic and a hydrophobic component and powdered activated carbon.

Experimental Investigation

The effect of three odour absorbing compounds and a superabsorbent polymer on the volatilisation of ethanethiol and thioacetic acid from aqueous solutions have been investigated using GC headspace techniques.

It was found that all three of the odour absorbing compounds and the superabsorbent polymer are effective (to a greater or lesser degree) at reducing the volatilisation of ethanethiol and thioacetic acid from aqueous solutions at 37° C.

The most effective system for reducing the volatilisation of ethanethiol and thioacetic acid from aqueous solutions at 37° C. was found to be a hydrophilic/hydrophobic zeolite blend combined with the superabsorbent polymer. This system showed around a 95% reduction of the ethanethiol peak and 100% reduction of the thioacetic acid peak.

Results indicate that at 37° C. and at concentrations of above 60 mg/5 ml the zeolite blend combined with polymer has comparable effectiveness with carbon black and polymer at suppressing the volatilisation of ethanethiol and thioacetic acid from aqueous solutions.

Analysis

A GC headspace analysis method was developed during the course of the investigations and used to quantify the levels of the odorous thiol compounds, thioacetic acid and ethanethiol, in the headspace above aqueous samples, with and without the presence of each of the absorbing compounds. The work found that two compounds—a zeolite blend and CW90 Zn salt—gave results which were comparable to activated carbon. Both compounds have the advantage over carbon black of being opaque/white, which should enable easier examination of stoma bags containing the compounds.

The report below, details further investigations conducted into the absorption properties of the hydrophobic and hydrophilic zeolites and the CW90 Zn salt at temperatures more closely resembling body temperature and in the presence of a superabsorbent polymer.

Objectives

To test the capabilities of the zeolites and the CW90 Zn salt to absorb $H_2S$, thioacetic acid, ethanethiol and skatole both in pure aqueous solutions and in the presence of a superabsorbent polymer.

Method

A stock solution of the odorous compounds $H_2S$, thioacetic acid, ethanethiol and skatole were made up at with 2 mg/ml in water. The samples were analysed using a Perkin Elmer XL40 gas chromatograph with a Zebron ZB-624 capillary GC column (30 m×32 mm×1.8 u) with an FID detector.

No signals associated with $H_2S$ and skatole were observed using the method. $H_2S$ was not detected by the FID detector and skatole was insoluble in water and its low volatility meant that the concentration in the headspace at 40° C. was negligible.

As a result, a second stock solution was prepared with 3 µl/ml thioacetic acid and 0.5 µl/ml ethanethiol in water only. 5 ml of the stock solution was then added to each of the following compounds:

TABLE 1

Summary of the solutions prepared, detailing the odour absorbing compound employed, its quantity and the quantity of superabsorbent polymer.

| Solution | Odour absorbing compound | Mass of compound (mg) | Mass of superabsorbent polymer (mg) |
|---|---|---|---|
| 1 | None | 0 | 0 |
| 2 | None | 0 | 25 |
| 3 | Activated Carbon | 67 | 0 |
| 4 | Activated Carbon | 62 | 28 |
| 5 | Zeolite Blend | 62 | 0 |
| 6 | Zeolite Blend | 59 | 25 |
| 7 | Zeolite Hydrophobic | 60 | 0 |
| 8 | Zeolite Hydrophobic | 65 | 25 |
| 9 | Zeolite Hydrophilic | 60 | 0 |
| 10 | Zeolite Hydrophilic | 58 | 26 |
| 11 | Cw90 Zn salt | 60 | 0 |
| 12 | Cw90 Zn salt | 60 | 24 |

The GC analysis set up was as follows for all samples:
Injection port temperature: 140° C.;
Carrier gas ($H_2$) pressure 8 psi;
Oven program:
 40° C. isocratic for 5 min;
 Ramp to 90° C. at 10° C./min;
 isocratic at 90° C. for 2 min;
FID detector temperature: 240° C.
Headspace sampling was carried out as follows:
Equilibrium time 7 minutes with shaking;
Pressurisation 0.5 minutes;
Injection 0.1 minutes;
Withdrawal 0.1 minutes;
Oven temperature 37° C.;
Needle 60° C.;
Transfer line 60° C.

Blank Results (Solutions 1+2)

Figure 4:
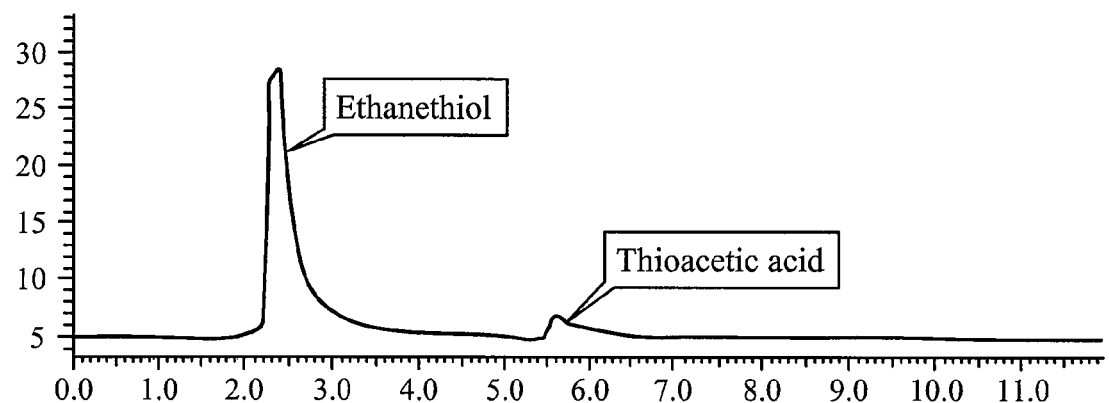
FIG. 4 is a GC chromatogram of solution 1-3 µl/ml thioacetic acid and 0.5 µl/ml ethanethiol in water.

Analysis of aqueous solution containing 3 µl/ml thioacetic acid and 0.5 µl/ml ethanethiol resulted in peaks at ~2.5 minutes for ethanethiol and 5.75 minutes for thioacetic acid, the results are shown in FIG. 4

Figure 5:
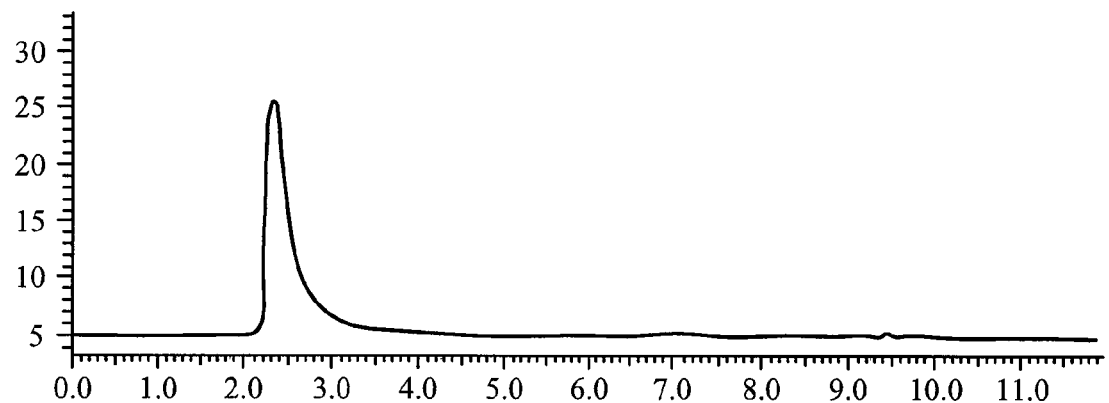
FIG. 5 is GC chromatogram of solution 2—aqueous solution containing superabsorbent polymer.
Figure 6:
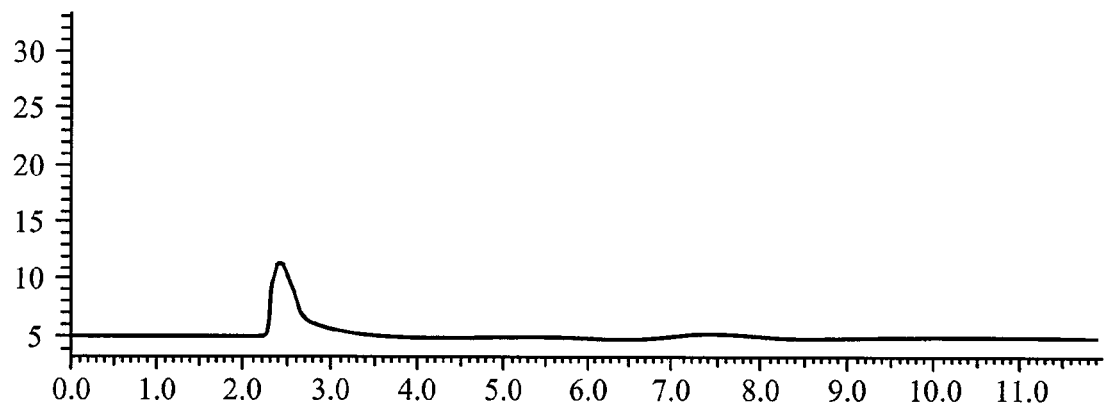
FIG. 6 is a GC chromatogram of solution 3—containing activated carbon.
Figure 7:
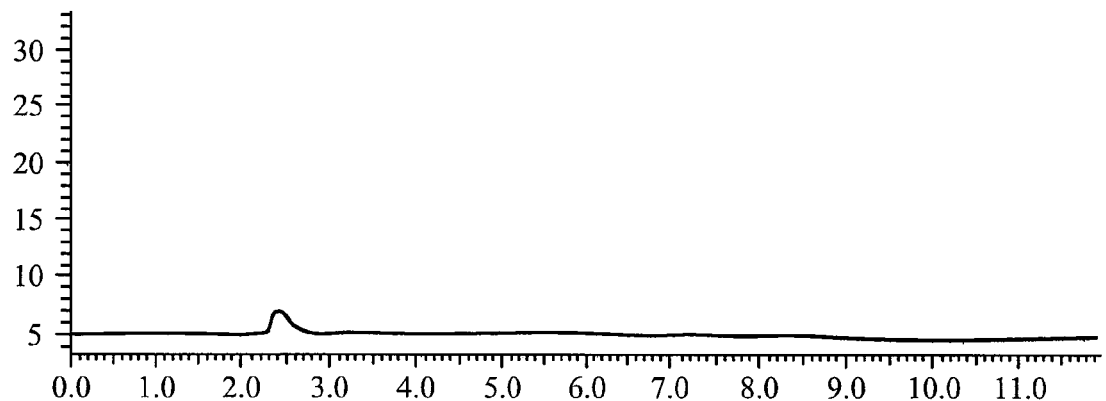
FIG. 7 is a GC chromatogram of solution 4—containing activated carbon and superabsorbent polymer.
Figure 8:
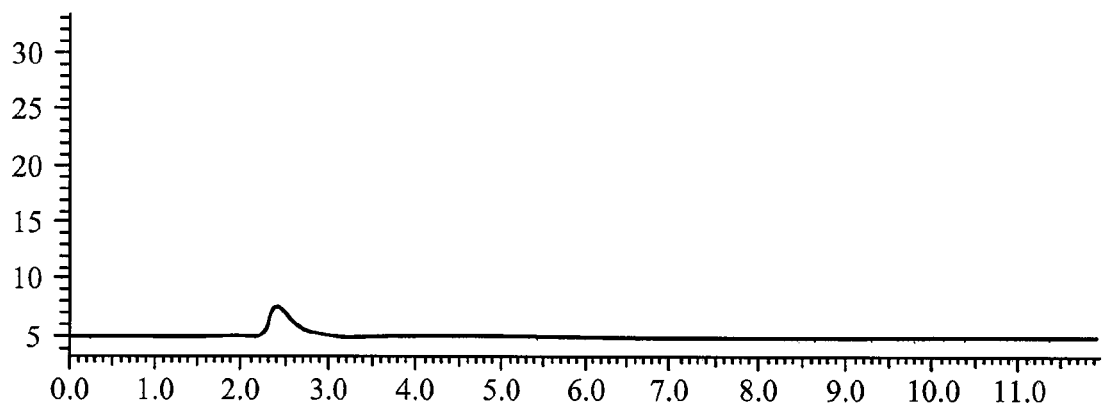
FIG. 8 is a GC chromatogram of solution 5—containing zeolite blend.
Figure 9:
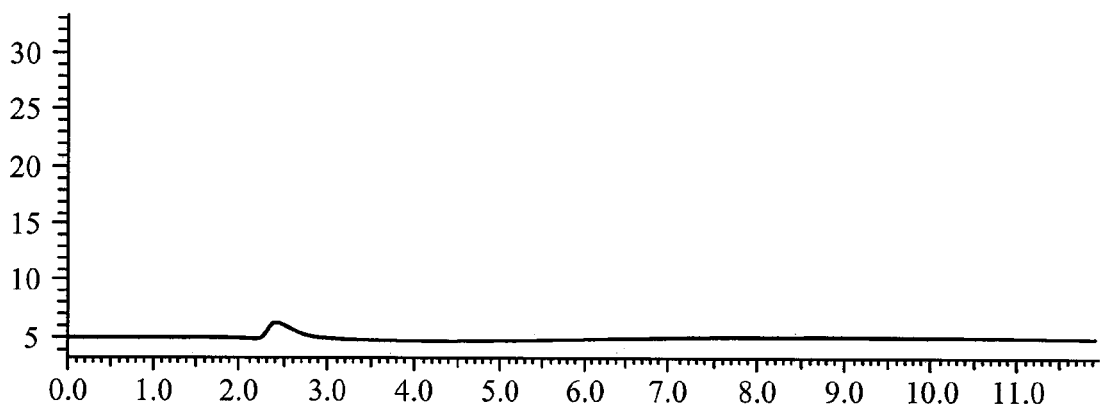
FIG. 9 is a GC chromatogram of solution 6—containing zeolite blend and super absorbent polymer.
Figure 10:
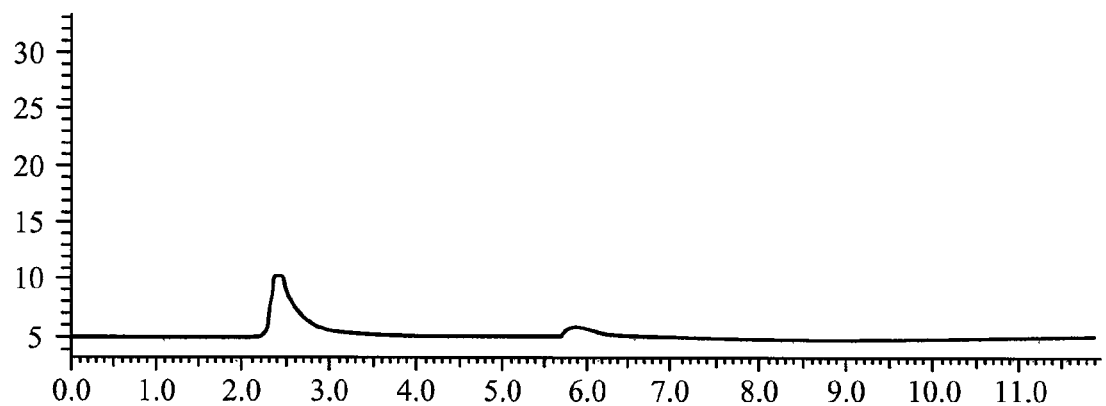
FIG. 10 is a GC chromatogram of solution 7—containing hydrophobic zeolite.
Figure 11:
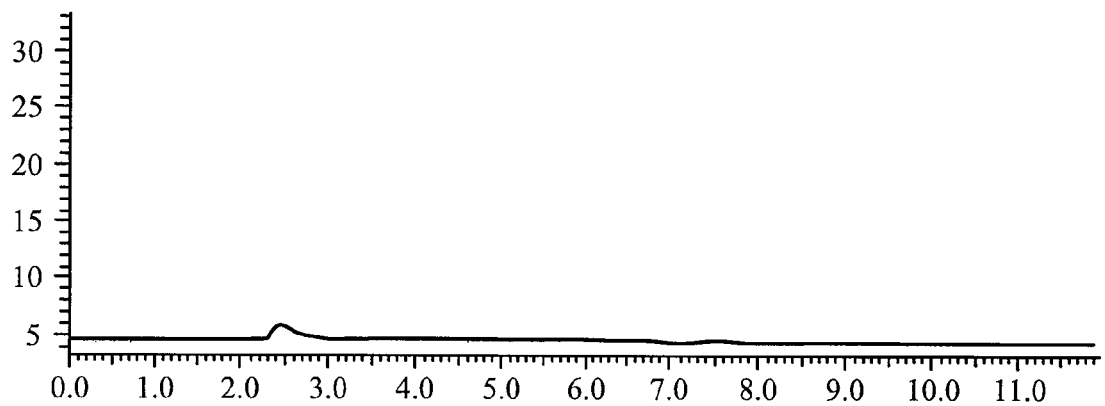
FIG. 11 is a GC chromatogram of solution 8 containing hydrophobic zeolite and super absorbent polymer.
Figure 12:
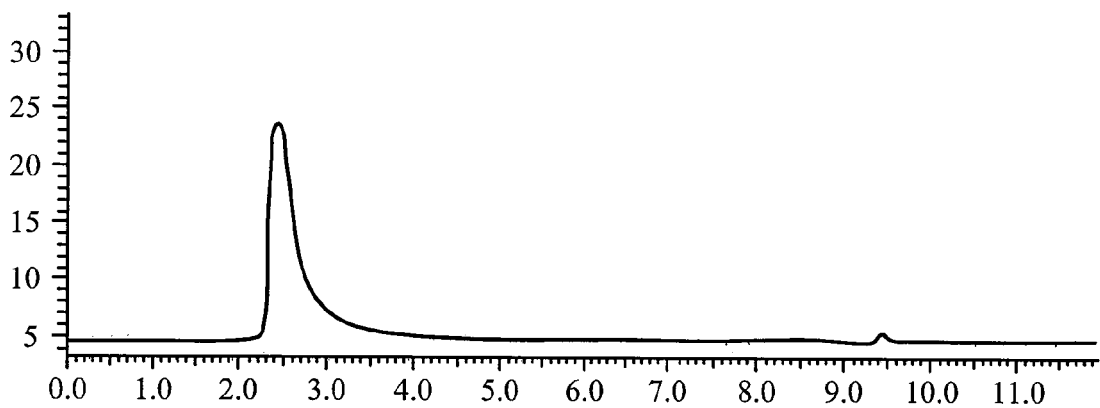
FIG. 12 is a GC chromatogram of solution 9 containing hydrophilic zeolite.
Figure 13:
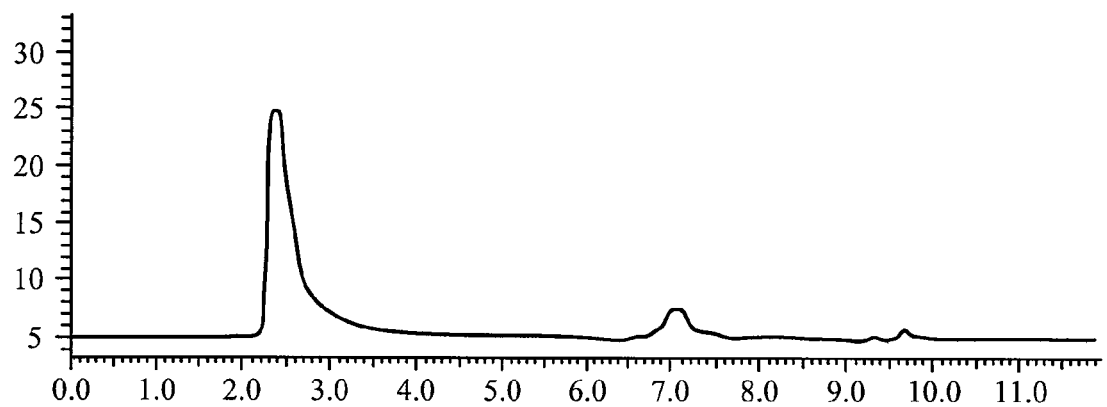
FIG. 13 is a GC chromatogram of solution 10 containing hydrophilic zeolite and superabsorbent polymer.
Figure 14:
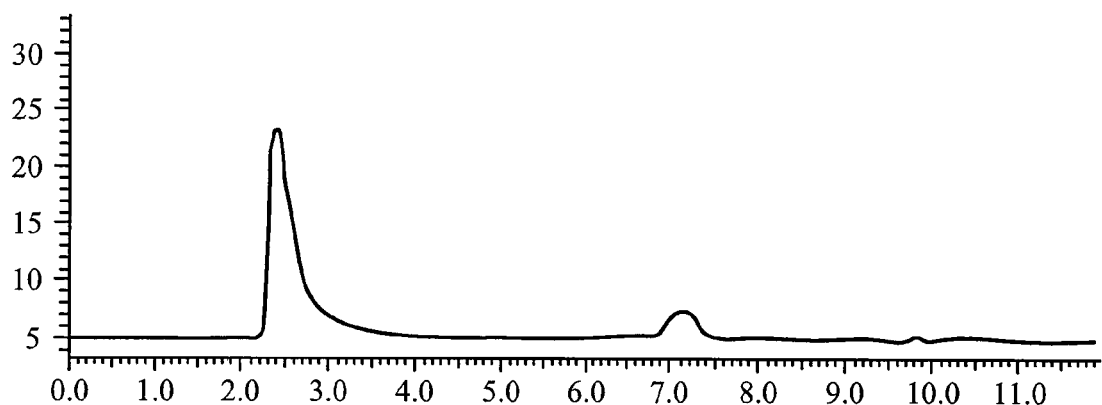
FIG. 14 is a GC chromatogram of solution 11 containing CW 90 Zn salt.
Figure 15:
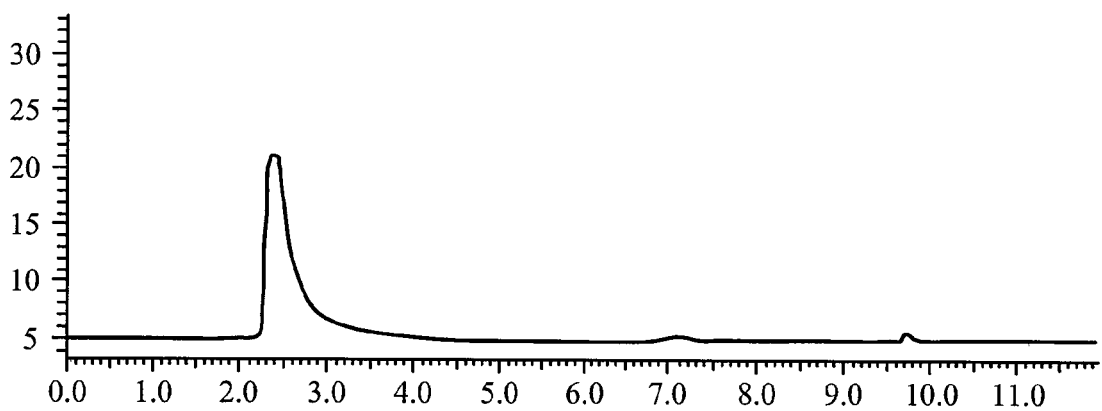
FIG. 15 is a GC chromatogram of solution 12 containing CW 90 Zn salt and superabsorbent polymer.

The same aqueous solution when added to 25 mg of superabsorbent polymer showed that the polymer itself had some odour absorbing qualities without the presence of any odour absorbing compounds, as shown in FIG. 5. The polymer was more effective at absorbing thioacetic acid than ethanethiol.

Summary of Results

| Solution | Compounds | Percentage decrease of ethanethiol peak (%) | Percentage decrease of thioacetic acid peak (%) |
|---|---|---|---|
| 3 | Carbon | 74 | 90 |
| 4 | Carbon + Polymer | 91 | 100 |
| 5 | Zeolite Blend | 89 | 100 |
| 6 | Zeolite Blend + Polymer | 95 | 100 |
| 7 | Zeolite Hydrophilic | 32 | 100 |
| 8 | Zeolite Hydrophilic + | 32 | 100 |
| 9 | Zeolite Hydrophobic | 80 | 50 |
| 10 | Zeolite Hydrophobic + | 96 | 100 |
| 11 | Cw90 Zn salt | 32 | 50 |
| 12 | Cw90 Zn salt + Polymer | 40 | 100 |

Effect of Concentration

The effect of the concentration of the absorbing compounds and the polymer on the level of odours compound absorption were also investigated. 5 ml of the stock solution containing ethanethiol and thioacetic acid was added to vials containing masses of odour absorbing compounds ranging from ~20 mg to ~150 mg. The results are displayed in the tables below. Note: all experiments on the absorbing compounds were performed in aqueous solutions without polymer.

Activated Carbon:

| Mass of compound (mg) | Percentage decrease of ethanethiol peak | Percentage decrease of thioacetic acid peak |
|---|---|---|
| 27 | 87 | 100 |
| 39 | 87 | 100 |
| 63 | 93 | 100 |
| 103 | 100 | 100 |

Zeolite Blend:

| Mass of compound (mg) | Percentage decrease of ethanethiol peak | Percentage decrease of thioacetic acid peak |
|---|---|---|
| 22 | 53 | 100 |
| 40 | 80 | 100 |
| 59 | 91 | 100 |
| 101 | 98 | 100 |

Zeolite Hydrophobic:

| Mass of compound (mg) | Percentage decrease of ethanethiol peak | Percentage decrease of thioacetic acid peak |
|---|---|---|
| 19 | 53 | 50 |
| 43 | 77 | 75 |
| 60 | 83 | 75 |
| 102 | 95 | 95 |

Zeolite Hydrophilic:

| Mass of compound (mg) | Percentage decrease of ethanethiol peak | Percentage decrease of thioacetic acid peak |
|---|---|---|
| 19 | 7 | 100 |
| 40 | 20 | 100 |
| 60 | 20 | 100 |
| 100 | 20 | 100 |

Cw 90Zn salt:

| Mass of compound (mg) | Percentage decrease of ethanethiol peak | Percentage decrease of thioacetic acid peak |
|---|---|---|
| 26 | 0 | 50 |
| 50 | 20 | 50 |
| 76 | 73 | 90 |
| 112 | 89 | 95 |

Superabsorbent gel:

| Mass of compound (mg) | Percentage decrease of ethanethiol peak | Percentage decrease of thioacetic acid peak |
|---|---|---|
| 32 | 13 | 100 |
| 55 | 27 | 100 |
| 80 | 40 | 100 |
| 150 | 33 | 100 |

The performance of the absorbing compounds identified as solutions 3 to 12 are detailed in FIGS. 6 to 15 respectively.

Figure 16:
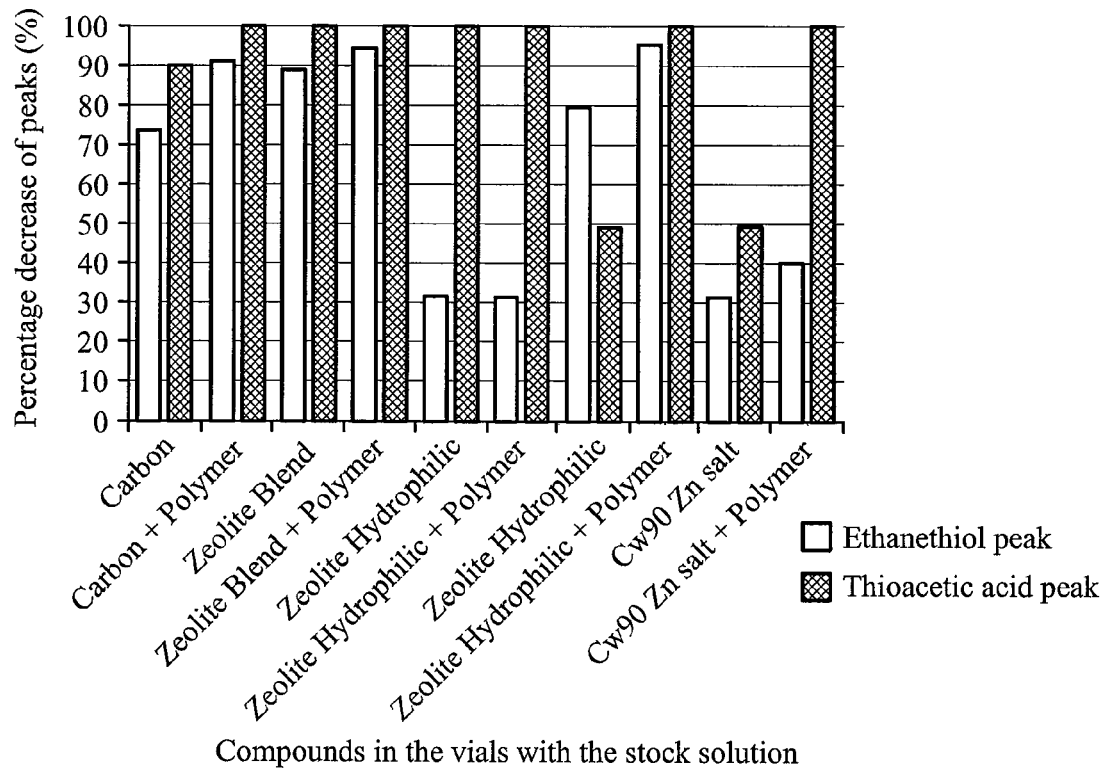
FIG. 16 is a graph of the percentage decrease of ethanethiol and thioacetic acid peaks for solutions 3 to 12.
Figure 17:
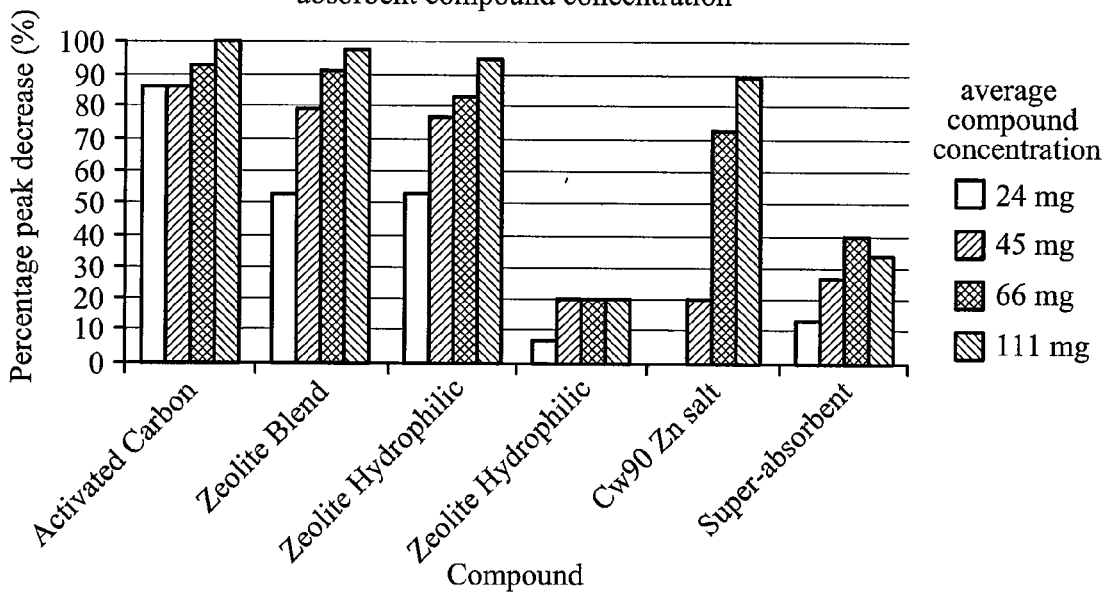
FIG. 17 is a graph of the percentage decrease of ethanethiol peak with increasing absorbent compound concentration.
Figure 18:
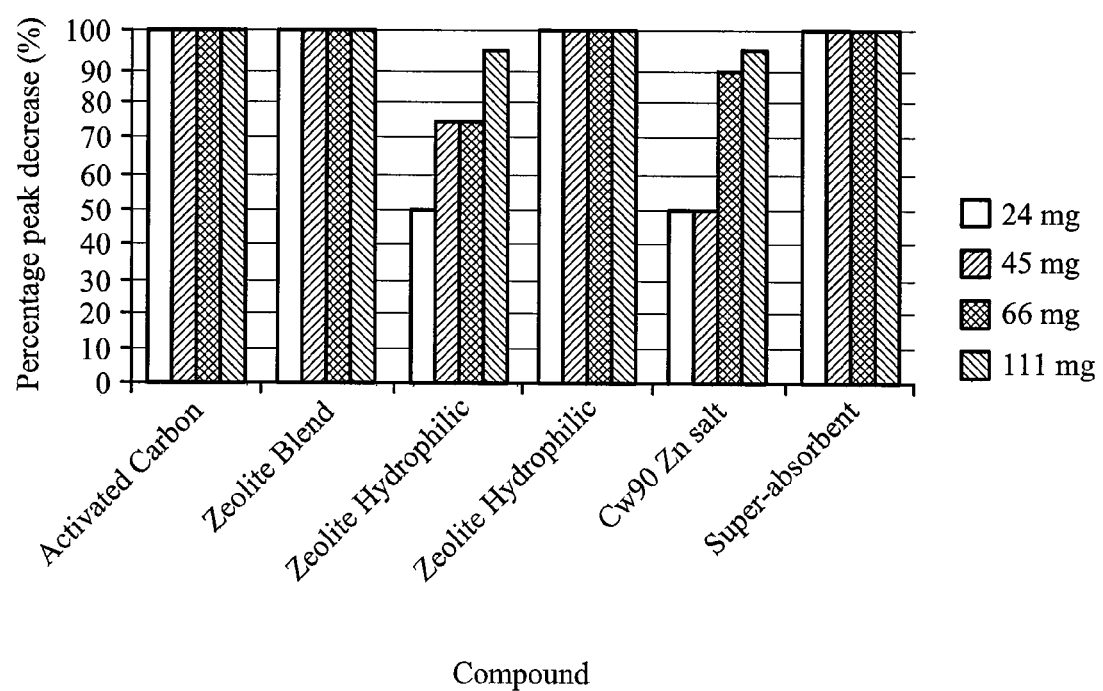
FIG. 18 is a graph of the percentage decrease of thioacetic acid peak with increasing absorbent compound concentration.

A summary of the percentage decrease of the ethanethiol and thioacetic acid peaks for solutions 1 to 12, based on the gas chromatography results of FIGS. 4 to 15 are shown in FIG. 16. The effect of the percentage decrease of the ethanthiol peak with increasing absorbent compound concentration is illustrated in FIG. 17 and the percentage decrease of thioacetic acid peak with increasing absorbent compound concentration is shown in FIG. 18.

CONCLUSIONS

No signals associated with $H_2S$ or skatole were observed using the GC headspace method. $H_2S$ was not detected by the FID detector and skatole was insoluble in water and its low volatility meant that the concentration in the headspace at 40° C. was negligible.

All the odour absorbing compounds reduced the peak height of ethanethiol and thioacetic acid compared to the blank, solution 1. The polymer also reduced the peak heights of ethanethiol by 20% and thioacetic acid by 90%.

Almost all the odour absorbing compounds showed enhanced peak reduction of ethanethiol and thioacetic acid with the presence of the superabsorbent polymer, the hydrophilic zeolite was the only compound which showed little to no enhancement of ethanethiol absorption by addition of polymer.

The present results indicate that the hydrophobic zeolite is more effective at reducing the ethanethiol peak than the thioacetic acid peak, whilst the hydrophilic zeolite shows the opposite effect and is much less effective at reducing ethanethiol, but effective at reducing the thioacetic acid peak.

The Zeolite blend containing both hydrophilic and hydrophobic forms (solution 5) absorbed more ethanethiol and thioacetic acid than the individual zeolites themselves.

The Zeolite blend (solution 6) combined with the superabsorbent polymer appears to be the most effective system for reducing the volatilisation of ethanethiol and thioacetic acid from aqueous solutions at 37° C. The solution showed ~95% reduction of the ethanethiol peak and 100% reduction of the thioacetic acid peak. The blend was successful because the hydrophobic zeolite had a greater effect on the absorption of ethanethiol and the hydrophilic zeolite a greater effect on the absorption of thioacetic acid.

At ~37° C. the performances of the zeolite blend and activated carbon appear to be roughly comparable. Activated carbon is more effective at the lower concentrations (~20 mg in 5 ml) at reducing the volatilisation of ethanethiol and thioacetic acid, but at higher concentrations (~60-100 mg) the zeolite blend performs equally as well.

Cw 90 Zn salt was the least effective of the three compounds tested and showed only minor reductions on the levels of ethanethiol. Reductions in the thioacetic acid peak height were observed. At higher concentrations, in aqueous solutions, the Cw 90 Zn salt performs relatively well suppressing both the ethanethiol and thioacetic acid peaks. However, in the presence of the polymer it performed less well, possibly indicating an inhibiting effect of the polymer on the salt's performance.

Generally, increasing the concentration of the odour absorbing compound decreased the volatilisation of ethanethiol and thioacetic acid. The exception was the hydrophilic zeolite, which reached a plateau of ethanethiol reduction at ~20%.

The invention claimed is:

1. A composition comprising: a polyacrylate superabsorbent an odor controlling agent and a zeolite blend; wherein the zeolite blend comprises a hydrophilic zeolite and a hydrophobic zeolite; and wherein the polyacrylate superabsorbent comprises sodium polyacrylate or calcium polyacrylate.

2. The composition of claim 1, wherein the zeolite blend is microporous.

3. The composition of claim 1, wherein the zeolite blend is natural or synthetic.

4. The composition of claim 1, wherein the hydrophobic zeolite comprises an ammonium zeolite.

5. The composition of claim 1, wherein the hydrophilic zeolite comprises sodium aluminosilicate.

6. A composition comprising:
a polyacrylate superabsorbent, an odor controlling agent, and a zeolite blend;
wherein the zeolite blend comprises a hydrophilic zeolite and a hydrophobic zeolite; and
wherein the zeolite blend comprises a naturally sourced zeolite selected from analcime, chabazite, clinoptilolite, heulandite, natrolite, phillipsite, and stilbite.

7. The composition of claim 1, wherein the zeolite blend is a powder.

8. The composition of claim 1, wherein the superabsorbent is coated with the zeolite blend.

9. The composition of claim 8, wherein the zeolite blend is bound to the superabsorbent by electrostatic forces.

10. A composition comprising:
a polyacrylate superabsorbent, an odor controlling agent, and a zeolite blend;
wherein the zeolite blend comprises a hydrophilic zeolite and a hydrophobic zeolite; and
wherein the zeolite blend comprises a particle size equal to or less than 0.15 mm.

11. The composition of claim 1, wherein the superabsorbent comprises a polymer of cross linked sodium polyacrylate or calcium polyacrylate.

12. The composition of claim 1, wherein the superabsorbent comprises fibers.

13. The composition of claim 1, wherein the superabsorbent comprises a starch or an alkaline metal polyacrylate.

14. The composition of claim 1, wherein the superabsorbent comprises a granular configuration.

15. The composition of claim 14, wherein the granular configuration of the polyacrylate superabsorbent is greater in size than that of the zeolite blend.

16. The composition of claim 1, wherein the odor controlling agent comprises hydrogen peroxide, bacterial growth inhibitor, sodium nitrate, or benzyl alkonium chloride.

17. The composition of claim 1, further comprising an odor counteractant, disinfectant, or a preservative.

18. The composition of claim 17, wherein the odor counteractant comprises a volcanic clay or activated carbon.

19. A composition comprising:
a polyacrylate superabsorbent, an odor controlling agent, and a zeolite blend;
wherein the zeolite blend comprises a hydrophilic zeolite and a hydrophobic zeolite;
wherein the composition further comprises activated carbon; and
wherein a weight % ratio of the activated carbon to zeolite blend is in the range of 0.01:1 to 0.05:1.

20. The composition of 18, wherein the activated carbon comprises coconut shell char.

21. The composition of claim 18, wherein the activated carbon comprises a surface area of substantially 1250 $m^2/g$.

22. The composition of claim 18, wherein the activated carbon is bound to the superabsorbent by electrostatic forces.

23. A composition comprising:
a polyacrylate superabsorbent, an odor controlling agent, and a zeolite blend;
wherein the zeolite blend comprises a hydrophilic zeolite and a hydrophobic zeolite; and
wherein the composition further comprises a metal impregnated activated charcoal.

24. The composition of claim 1, wherein the composition is housed within a water soluble film, a PVA film, a gel cap, a plastic straw or plastic wand, or a paper sachet.

25. The composition of claim 1, wherein the composition is formed as a tablet or a pellet.

26. An insert adapted for malodor control in a device, wherein the insert comprises the composition of claim 1.

27. The insert of claim 26, wherein the device is an ostomy bag.

* * * * *